United States Patent
Yeo et al.

(10) Patent No.: US 11,028,327 B2
(45) Date of Patent: Jun. 8, 2021

(54) PARTIAL TRIP SYSTEM FOR ETHYLENE FURNACE WITH GROUND FLARE

(71) Applicant: ExxonMobil Chemical Patents Inc., Baytown, TX (US)

(72) Inventors: Gregory E. Yeo, Houston, TX (US); Jennifer L. Port, Cypress, TX (US); Philippe J. Le Roy, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 6 days.

(21) Appl. No.: 16/519,162

(22) Filed: Jul. 23, 2019

(65) Prior Publication Data

US 2020/0048561 A1    Feb. 13, 2020

Related U.S. Application Data

(60) Provisional application No. 62/716,772, filed on Aug. 9, 2018.

(51) Int. Cl.
*C10G 9/20* (2006.01)
*C07C 5/327* (2006.01)

(52) U.S. Cl.
CPC .............. *C10G 9/206* (2013.01); *C07C 5/327* (2013.01); *C10G 2300/1081* (2013.01); *C10G 2300/4012* (2013.01); *C10G 2300/4056* (2013.01); *C10G 2300/4075* (2013.01); *C10G 2400/20* (2013.01)

(58) Field of Classification Search
None
See application file for complete search history.

(56) References Cited

U.S. PATENT DOCUMENTS

| | | | |
|---|---|---|---|
| 2005/0137440 A1* | 6/2005 | Bushuev | C10G 9/36 585/648 |
| 2016/0168478 A1 | 6/2016 | Spicer et al. | |
| 2017/0081594 A1 | 3/2017 | Spicer et al. | |

FOREIGN PATENT DOCUMENTS

WO    2017/052685 A    3/2017

* cited by examiner

*Primary Examiner* — Philip Y Louie

(57) ABSTRACT

Systems and methods are provided for performing a partial trip for an ethane steam cracker while reducing or minimizing ethane consumption in a ground flare system during the partial trip. In particular, a trip system is provided that reduces the firing on an ethylene furnace (such as a reduction into a range of 10% to 40% of normal firing) while also providing a reduced flow of feed to the furnace with dilution steam at a steam to hydrocarbon ratio similar to a ratio that is suitable during normal operation. The trip system can be actuated, for example, when the loss of circulating quench water to the water quench tower is detected.

20 Claims, 2 Drawing Sheets

PARTIAL TRIP SYSTEM FOR ETHYLENE FURNACE WITH GROUND FLARE

PRIORITY CLAIM

This application claims priority to and the benefit of U.S. Provisional Patent Application Ser. No. 62/716,772, filed Aug. 9, 2018, and is incorporated herein by reference.

FIELD

The invention relates to the field of thermal cracking hydrocarbons for the production of olefins, particularly low molecular weight olefins such as ethylene. More particularly the invention relates to methods and equipment for operating a steam cracking furnace with a ground flare during a partial trip event.

BACKGROUND

Thermal cracking of hydrocarbon feeds in the presence of steam ("steam cracking") is a commercially important technology for producing light olefins such as ethylene, propylene, and butadiene. Steam cracking furnaces for carrying out a steam cracking process generally include a convection section, a radiant section located downstream of the convection section, and a quenching stage located downstream of the radiant section with respect to the flow of hydrocarbon feeds. At least one burner is included in the steam cracking furnace for providing heat to the convection and radiant sections. The burner(s) are located in at least one firebox, the firebox being proximate to the radiant section, with the convection section being located downstream of the radiant section with respect to the flow of heated combustion gases produced by the burner. Tubular coils (sometimes referred to as process tubes) are utilized for conveying the hydrocarbon feed, steam, and mixtures thereof through the furnace's convection section ("convection tubes") and radiant section ("radiant tubes"). Hydrocarbon is cracked in the process tubes to produce a steam cracked effluent. The steam cracked effluent is quenched downstream of the radiant section, and is conducted away for further processing to produce the light olefins.

An example of further processing to produce light olefins can be the use of a water quench tower to recover olefins in the steam cracked effluent. The effluent enters low in the water quench tower and then rises toward the top of the tower. Flowing down the tower (i.e. counter-current) is a large volume of cooled process condensate (quench water). The high volume quench water stream is provided by a series of large pumps. For a cost-efficient and energy-efficient facility design, it is common for most or all of these pumps to be driven by electric motors.

The tower typically has internals such as trays or packing to provide efficient contacting between the steam cracked effluent and the quench water. The large volume of circulating quench water condenses the dilution steam from the steam cracked effluent, and cools the vapor to a temperature in the range of from 75° F. to 150° F. (~25° C. to ~65° C., where the tilde indicates "approximately"). A quenched stream, which comprises a major amount of hydrocarbon, is recovered and then compressed to a higher pressure at which the separation of individual product components can be effected.

The compression of the quenched hydrocarbon stream is achieved using a large, multi-stage centrifugal compressor known as the Process Gas Compressor ("PGC"). These compressors are typically driven by a steam turbine. In a modern, large capacity ethylene plant the power demand of the PGC can approach 100,000 hp (~73.5 MW). PGC trains are very sophisticated, expensive sets of machinery and thus are typically equipped with automatic shutdown systems that operate when a potentially unstable condition is detected on the machine. Excessive vibration of the compressor/turbine set is one such condition, as is high temperature of the gas entering the compressor.

A byproduct of the cracking reactions that take place in the furnace is the deposition of a carbonaceous material (typically called "coke") on the inner surfaces of the radiant tubes. When the coke thickness in the tubes becomes sufficient to create either a hydraulic constraint on the furnace or to generate a radiant tube metal temperature constraint on the furnace, feed is withdrawn from the furnace, air is added, and the coke is controllably combusted. This operation, known as decoking (or steam-air decoking) is generally conducted periodically, e.g., at an interval in a range of about 20 to 90 days, depending on the furnace design and the type of feed being cracked.

Cracking furnaces are typically equipped with emergency shutdown systems (trip systems) that automatically take the furnace to a quiescent condition when a potentially unstable condition is detected on the furnace. Historically, these trip systems shut off all fuel to the furnace. However it was found that under such a trip (100% trip of fuel) the radiant tubes contracted over the inside coke layer and would sometimes fracture from, e.g., thermal shock. This behavior is especially common in the case of steam cracking an ethane feed ("ethane cracking"), due to the hardness of the coke produced during ethane cracking. After fracture, the fractured tubes can allow the back-flow of hydrocarbons from the downstream facilities, which can potentially lead to equipment damage.

In order to reduce or minimize the potential for fracture of the radiant tubes, modern furnaces for steam cracking often have a steam partial trip (or, "partial trip"). During a steam partial trip, when a potentially unsafe condition is detected, the fuel rate to the furnace is decreased into a range of about 10% to 40% of the normal firing value. Additionally, the hydrocarbon feed is removed from the furnace. Steam remains flowing through the furnace coils, however, and the radiant coils remain at sufficiently high temperatures to prevent fracture over the coke layer inside the tubes. To achieve the desired temperatures and flow conditions in the furnace during a steam partial trip requires a steam rate that is generally higher than the dilution steam rate used during cracking operations. This higher steam rate can be, for example, sufficient to hydraulically load the furnace tubes and provide an acceptable minimum flow rate in each tube. If the steam partial trip does not substantially eliminate the potentially unstable condition, then the furnace can fully trip (100% fuel shut off).

Ethylene plants are typically equipped with a flare system to safely combust excess gas that can be generated, for example, by the shutdown of the PGC. In the case of a PGC shutdown, gas continues to enter the quench tower from the furnaces and the quench tower pressure rises. At a pre-set pressure, relief valves on the quench tower will open to the flare system to prevent damage to the quench tower from excessively high pressures.

Historically ethylene plants used elevated flares, where large volumes of gas were combusted in a single, large flare-tip. Flare-tips were designed to facilitate the mixing of air with the flare-gas, but the volume and composition of gas flared following a PGC trip often leads to the generation of significant smoke at the flare-tip. Addition of steam to the flare gas proved effective at suppressing flare tip smoking, but the cooling/dilution effect of the steam decreases hydrocarbon combustion efficiency. Thus instead of flare gas being completely combusted to $CO_2$ and $H_2O$, some incompletely combusted hydrocarbons can be released to the atmosphere. These compounds are considered air pollutants and can contribute to the formation of photochemical smog.

To achieve smokeless flaring while also achieving high hydrocarbon destruction efficiency, modern ethylene plants are often equipped with a "ground flare", which comprises a large number of small burner tips. Each burner tip is designed to inspirate sufficient air to burn with little or no smoke emission. A ground flare covers a significant area of real-estate, and is typically equipped with radiation barrier walls around its perimeter.

Ground flares rely on the flare gas having a sufficiently high heating value, often measured in Btu/SCF (British Thermal Units [energy] per Standard Cubic Feet [volume]), to assure full combustion of the contained hydrocarbons and also to allow each individual burner tip to light from the flame on the adjacent burner tip (so-called "cross-lighting"). A common requirement is to have a flare gas heating value of no lower than 800 Btu/SCF (~30 $MJ/m^3$). Unfortunately, during a steam partial trip where the process gas compressor is also shut down, the steam used to protect the furnace tubes is added to the flare gas. Doing so can significantly lower the heating value of the flare gas. In order to maintain a target heating value for the flare gas, substantial amounts of additional feed and/or fuel have to be added to the flare gas.

What is needed is a furnace design and process of operating a furnace that reduces or prevents thermal shock of the furnace tubes during a steam partial trip while also reducing or minimizing the amount of fuel that needs to be added to the ground flare system to maintain a desired heating value in the flare gas during the steam partial trip.

U.S. Patent Application Publication No. 2017/0081594 describes a process and apparatus for reducing thermal shock in a steam cracking furnace. The apparatus includes a blower and a blower bypass conduit that provide separate fluid communication paths for flue gas from the convection section to a natural draft flue gas stack. When a blower shut down event is detected, the firing rate of the furnace can be reduced and at least a portion of the flue gas can be redirected to the blower bypass conduit.

SUMMARY

In various aspects, systems and methods are provided for performing a partial trip for a steam cracker, such as an ethane steam cracker while reducing or minimizing ethane consumption in a ground flare system during a partial trip. In particular, a trip system is provided that decreases ethylene furnace firing (such as a reduction into a range of about 10% to about 40% of normal firing) while also decreasing the flow of feed to the furnace at a steam to hydrocarbon ratio similar to a ratio that is suitable for normal operation. For example, during a partial trip, the volume ratio of steam to hydrocarbon in the feed to the process coils can be about 0.2 to about 0.5, which is similar to suitable steam to hydrocarbon volume ratios during normal operation of a steam cracker. The reduced flow rate of feed to the process coils during the partial trip can correspond to roughly 30% to 60% of the flow rate to the process coils during normal operation of the steam cracker. By passing a feed including steam and hydrocarbon into the process tubes during the partial trip, the amount of fuel burned in the ground flare system can be substantially reduced relative to performing a partial trip using only steam as the feed to the process tubes.

In various aspects, the ability to perform a partial trip of a steam cracker can be dependent on the ability of the furnace to draw sufficient draft when power is not available to induce draft using a blower. For example, the flue gas stack for the furnace can include a secondary flow path that opens if the blower is not able to provide an induced draft. This secondary flow path can allow for natural draft from the furnace, so long as the flue gas stack has a suitable height to facilitate a natural draft. The partial trip can be triggered, for example, based on detection of a loss of operation in a component downstream from the quench system.

DETAILED DESCRIPTION

Figure 1:
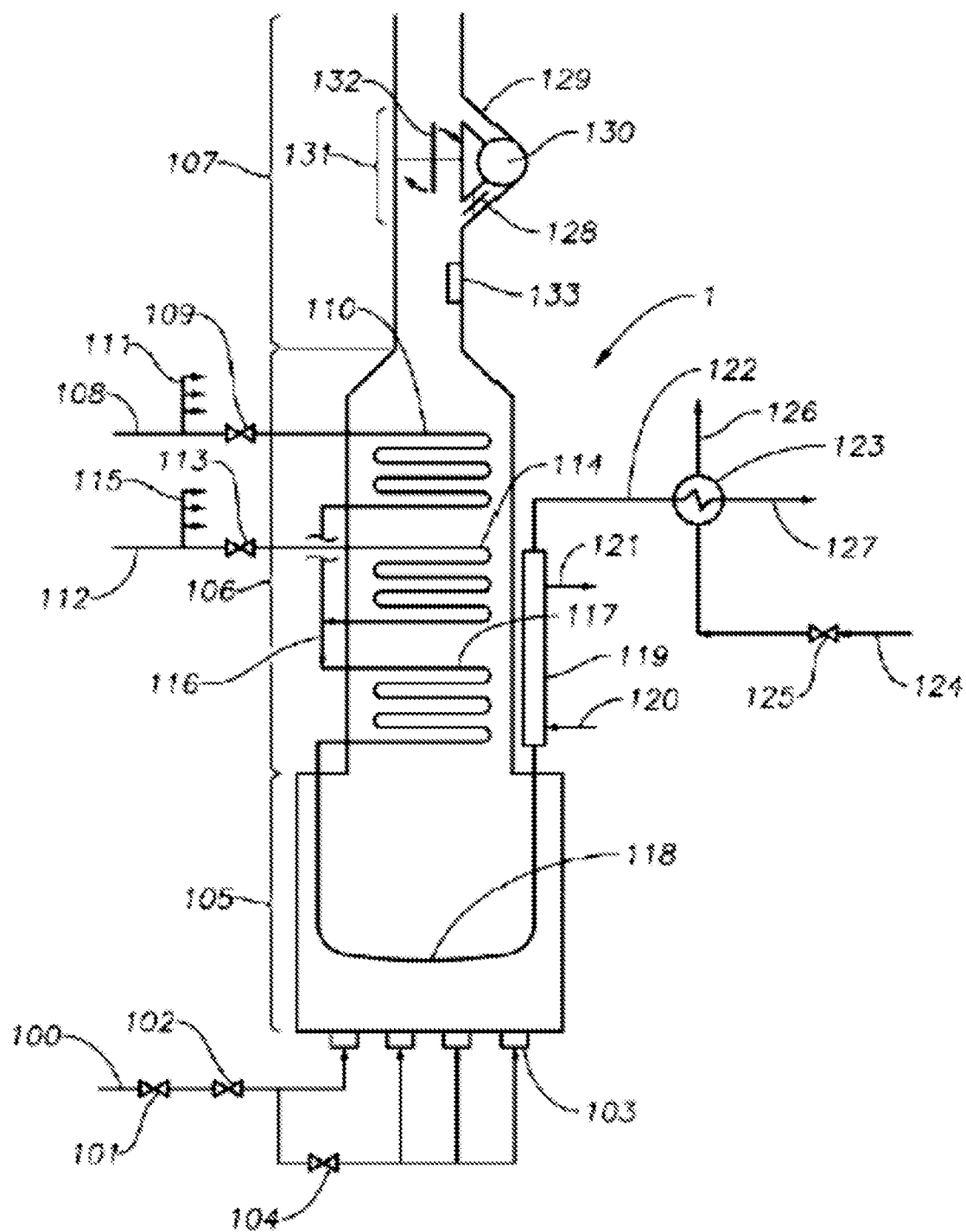
FIG. 1 schematically shows an example of a configuration for a steam cracker furnace.

In various aspects, systems and methods are provided for performing a steam partial trip for an ethane steam cracker while reducing or minimizing ethane consumption in a ground flare system during a steam partial trip. In particular, a trip system is provided that reduces the firing on an ethylene furnace (e.g., to achieve an amount of firing in a range of about 10% to 40% of normal firing) while also providing a reduced flow of feed to the furnace with dilution steam at a steam to ethane ratio similar to the ratio during normal operation. This can reduce or minimize the ethane required in the flare gas in order to achieve the minimum required heating value during a steam partial trip. The trip system can be actuated, for example, when the loss of circulating quench water to the water quench tower is detected. Such a contingency can lead to the shutdown of the PGC and the relief of all furnace effluent to the flare through the quench tower overhead relief valves.

In order to protect the process coils (process tubes) during a partial trip of a steam cracker furnace, the firing rate of the furnace can be reduced while enough gas is passed through the process coils to reduce or minimize fracturing of the coils due to thermal shock. Conventionally the gas that is passed into the process coils during a furnace trip is steam, in order to minimize the risk of radiant tube fractures occurring while feed is in the coils. This can also reduce or minimize the needed firing rate for the furnace by reducing or minimizing temperature drop within the process coils due to the endothermic cracking reactions. Unfortunately, the amount of steam that is conventionally required to maintain the temperature of the process coils must be larger than the amount of dilution steam that is typically included in the feed during normal operation. When this steam is subsequently passed into the ground flare system, a substantial amount of additional hydrocarbon has to be added to the ground flare to achieve a desired or target energy value for the flare gas.

It has been discovered that when the feed for the process coils corresponds substantially to ethane, the target temperature for avoiding damage to the process coils due to thermal shock can be low enough so that any cracking of the ethane feed can be minimal. As a result, a feed mixture of ethane and steam similar that is suitable for cracking under full temperature conditions can be used during a steam partial trip without causing substantial amounts of endothermic cracking reactions to occur. Using a feed mixture including ethane during a partial trip of an ethane cracking furnace can reduce, minimize, or possibly eliminate the amount of supplemental hydrocarbons that need to be subsequently added to the flare gas. In addition to reducing the amount of supplemental hydrocarbon, using a feed mixture containing ethane during a partial trip can also provide improved reliability for the flare enrichment system. A typical ethylene plant can include a plurality of furnaces. Under the conditions that can lead to a partial trip, a furnace triggering a partial trip can utilize a reduced or minimized amount of flare enrichment gas. In the event that any furnaces do not enter a partial trip state, the capacity of the flare enrichment system can be substantially devoted to compensating for the fuel value from those furnaces that are not in the partial trip state. In aspects where all of the furnaces associated with an ethylene plant enter the partial trip state, the amount of additional hydrocarbon provided to the ground flare system can be an order of magnitude less than what would otherwise be needed.

In some aspects involving an ethylene plant that uses a ground flare, the volume of hydrocarbon needed to meet a flare-gas minimum heating value can be reduced or minimized if, when quench water circulation is lost, the furnaces have a partial firing trip mode where: a) Furnace firing is reduced to the same (or a substantially similar) firing rate employed in a conventional "steam partial trip"; b) when a loss of quench water circulation is detected, feed remains in the furnace at the normal steam to feed ratio; and c) the feed rate to the furnace under the partial trip for loss of quench water circulation is set to provide coil (i.e., process tube) temperatures of about 1000° F. (~538° C.) or more, or about 1300° F. (~700° C.) or more, so that the probability of fracturing radiant coils during the partial trip is minimized. For example, the temperature of the process coils during a partial trip can be roughly 538° C. to 730° C.

In various aspects, the systems and methods described herein can be used for steam cracking processes where the feed is substantially composed of ethane. A feed substantially composed of ethane can correspond to a feed where 50 wt. % or more of the $C_{2+}$ hydrocarbons and/or $C_{2+}$ hydrocarbonaceous compounds in the feed correspond to ethane, or 70 wt. % or more, or 90 wt. % or more, or 95 wt. % or more, or 98 wt. % or more, such as up to 100 wt. %. Hydrocarbonaceous compounds correspond to compounds containing carbon and hydrogen that also include one or more heteroatoms typically found in a petroleum-based hydrocarbon fraction. Examples of heteroatoms include sulfur, nitrogen, and oxygen. It is noted that the above definition does not restrict the amount of methane in the feed. Methane is less reactive than ethane under steam cracking-type conditions. While methane is typically not desirable as part of a feed for steam cracking, the presence of methane does not strongly impact the suitability of a feed substantially composed of ethane for performing the methods described herein.

In addition to ethane (or other hydrocarbon), during normal operation for production of olefins and/or other steam cracking products, the feed to the process tubes in a steam cracking reactor can also include steam as a diluent. After addition of any diluent steam, the volume ratio of steam to total hydrocarbon (and/or the volume ratio of steam to total $C_{2+}$ hydrocarbon) in the feed to the process tubes can be from about 0.2 to about 0.5. When the hydrocarbon portion of the feed is substantially composed of ethane, the volume ratio of steam to ethane can be from about 0.2 to about 0.5. In some aspects where a mixture of ethane and steam is used as the feed to the process tubes during a partial trip event, the ratio of steam to ethane can be from about 0.2 to about 0.5, such as substantially the same ratio as used during normal operation for production of olefins.

During a partial trip event, the amount of fuel delivered to the furnaces per unit time (fuel rate) can correspond to 10% to 40% of the amount of fuel (based on heating value) delivered to the furnaces during normal operation, or 20% to 33%.

During a partial trip event, the amount of feed (corresponding to steam plus ethane and/or other hydrocarbon) delivered to the process tubes can also be reduced relative to the amount of feed used during typical operation for production of olefins. In various aspects, the ratio of the amount of feed (ethane plus steam) delivered to the process tubes during a partial trip event relative to the amount of feed during normal operation for olefin production can be from 0.3 to 0.6, or 0.3 to 0.5, or 0.4 to 0.6. This ratio can correspond to, for example, a volume of feed per unit time. The reduced feed rate during a partial trip can be sufficient to assist with maintaining the temperature of the radiant coils. Additionally or alternately, the reduced feed plus steam rate can be sufficient to entrain any radiant coke that can spall off the tubes during the partial trip. Entraining the radiant coke that chips or breaks off from the walls of the tubes during a partial trip can reduce or minimize the likelihood of the radiant tube becoming plugged due to such coke. This can potentially avoid a full furnace trip and/or a delayed restart while the radiant tubes are cleared.

During a partial trip event, the feed introduced into the process tubes passes through the process tubes and becomes an exit stream. The exit stream (or at least a portion thereof) is then directed into the ground flare system. In a conventional system where steam is the only feed component during a partial trip, a substantial amount of additional fuel has to be added to the ground flare system in order to allow the ground flare system to operate with smokeless flaring. By contrast, using a feed comprising ethane (and/or other hydrocarbon) plus steam during a partial trip event can allow the ground flare system to operate in a desired manner without introduction of additional fuel. Alternatively, the amount of additional fuel introduced into the ground flare system can have a heating value that is less than the heating value of the exit stream. For example, the exit stream (or at least the portion of the exit stream introduced into the ground flare system) can have a heating value of about 700 BTU/SCF (about 26 MJ/m$^3$) or more, or about 800 BTU/SCF (about 30 MJ/m$^3$) or more, such as up to about 1000 BTU/SCF (about 37 MJ/m$^3$) or possibly still higher. Additionally or alternately, the additional fuel introduced into the ground flare system can have a heating value that is 25% or less than the heating value of the exit stream, or 15% or less, or 10% or less.

It is noted that a plurality of steam cracker furnaces may use a common ground flare system. In such a configuration, the benefit of using a feed including both ethane and steam during a partial trip can be magnified. For example, in a configuration where between six and twelve steam cracker furnaces share a single ground flare system, the amount of fuel used during a partial trip of all of the furnaces can be reduced by an order of magnitude or more. In a conventional system, introducing sufficient steam to reduce or minimize the likelihood of furnace plugging due to spall of coke during the partial trip means that the volume flow rate of steam into the process tubes can correspond to 40% or more of the total feed volume flow rate during typical operation. Introducing sufficient additional fuel into the ground flare system to increase the heating value of this steam can be substantial. Instead, in various aspects, the volume flow rate of gas that is needed to reduce or minimize plugging during a partial trip can be partially provided by ethane (and/or other hydrocarbons). This substantially increases the heating value of the feed into the process tubes during a partial trip and thereby substantially reduces (or even eliminates) the amount of additional fuel that needs to be introduced into the ground flare system.

Ethane Steam Cracking Process

In a steam cracking process with a hydrocarbon feed (such as a feed substantially composed of ethane), the hydrocarbon feed is preheated, mixed with dilution steam, and then further preheated (typically in the convection coils) to a temperature at which significant thermal cracking is about to commence. Hydrocarbon feeds can generally include one or more of ethane, propane, butane, naphtha, heavy gas oils, and crude oil. For a feed substantially composed of ethane, the temperature at which thermal cracking is about to commence may be in the range of from 1250° F. to 1350° F. (about 675° C. to about 730° C.). The preheated feed and dilution steam can be passed from the convection coils to the radiant coils where thermal cracking to produce olefins occurs. In the radiant section (also typically called a cracking zone), the feed and dilution steam mixture is rapidly heated to high temperatures, such as in a range of from 1550° F. to 1650° F. (about 845° C. to about 900° C.) for ethane cracking, to produce the desired product range.

Immediately following the radiant section the mixture is rapidly cooled to quench the thermal cracking reactions. Modern cracking furnace designs recover as much useful energy as possible from the cracked furnace effluent. A typical ethane cracking furnace heat recovery train may include heat exchangers to generate super-high-pressure (SHP) steam, such as steam at 1500 psig (—10.3 MPa-g) or higher, followed by additional heat exchanger to preheat high pressure boiler feed water (HPBFW), or furnace feed, or mixtures of furnace feed and dilution steam. The heat recovery train may also include heat exchangers to generate dilution steam from boiler feed water or treated process condensate. Regardless of the heat exchanger train employed, there is a lower limit to the furnace effluent temperature than can be achieved without fouling the heat exchangers in the system. In the case of ethane cracking, furnace effluent is generally not cooled below the range of about 350° F. to 400° F. (about 177° C. to about 204° C.).

The energy input to the furnace is provided by combusting a fuel stream in burners mounted in the radiant section. The hot flue gas generated by the burners is conducted away from the firebox through the convection section and away from the steam cracker via a flue gas stack. The flue-gas is exhausted from the convection section using an induced-draft fan. It is common for the induced draft fans of furnaces to be driven by electric motors. A negative pressure (also called "draft") is generated in the flue gas stack to facilitate proper combustion and flue gas removal. Additionally, the draft is maintained for safety reasons to prevent hot flue gas from exiting through any openings in the firebox, such as, at an open visual inspection port. Maintaining draft ensures ambient air flows in through any firebox openings instead of hot flue gas exiting the firebox anywhere other than out the stack.

In the case of an interruption of the power supply to a typical ethylene plant, one or more of the following may occur. The induced draft fans of the furnaces can lose power. This can cause flue-gas pressure inside the furnace to increase, resulting in a process instability. The furnace trip system can detect the potentially unstable condition and trip the furnace to steam partial trip conditions. Many furnaces can sustain such a condition with the induced draft fan stopped. An example of such a furnace is shown in FIG. 1, which is discussed in more detail below. To avoid nuisance trips, it is common to have short time delay (e.g. 60 seconds) from the time high flue-gas pressure is detected before the furnace is taken to the steam partial trip condition.

During conventional steam partial trip conditions, the furnace continues to pass steam to the transfer-line and eventually the quench tower. The steam rate can be greater than the steam rate during cracking operations, such as a rate sufficient to hydraulically load the furnace tubes and provide an acceptable minimum flow rate in each tube. However, if an interruption to the power supply has occurred, the pumps circulating quench water to the quench tower can lose power. With water no longer circulating, the steam entering the quench tower is not condensed, and the temperature of the quench tower overhead stream rises. The trip system on the PGC detects a high gas inlet temperature and shuts down the compressor to protect the machine. The pressure in the quench tower rises until the quench tower overhead relief valves open and direct the furnace effluent to the ground flare.

After the initial de-pressure of the PGC circuit and other affected sections of the plant, the main vapor stream entering the flare is steam flowing from the furnaces. At this point the heating value of the flare gas may fall below the minimum acceptable value. To prevent this, the plant can employ a flare-enrichment facility which detects low flare-gas heating value and adds a sufficient flow of hydrocarbon to the flare to re-attain the required flare-heating value. In the case of an ethane cracker, ethane feed may be used as the flare enrichment gas. However, since the furnaces at steam partial trip conditions can send more steam to the quench tower than during normal cracking operations, the required volume of ethane enrichment gas to the flare can be very high. It may even exceed the ethane feed rate required to run the plant at full capacity.

In contrast to a conventional steam partial trip, in various aspects, a mixture of dilution steam and ethane (or a feed substantially composed of ethane) can be passed into the process tubes during a partial trip event. Due to the lesser heat capacity of ethane, the total volume of gas passed into the process tubes may be greater when using ethane plus steam to maintain the temperature in the process tubes during a partial trip. However, at typical ratios of steam to ethane, the total amount of steam passed into the process coils during a partial trip event is reduced. The reduced amount of steam in combination with the additional ethane in the feed can reduce or minimize the amount of supplemental hydrocarbon needed in the flare gas during a partial trip event.

Example of Steam Cracking System Configuration

Referring now to FIG. 1, a non-limiting exemplary embodiment of a steam cracking furnace 1 is illustrated. Fuel comprising gas or liquid hydrocarbon fuel is provided via conduit 100 and through shut-off valve 101 and control valve 102. At least a portion of the fuel passes through valve 102 to at least one of a plurality of burners 103 that provide radiant heat to produce the desired products by steam cracking a hydrocarbon feed. A second portion of the fuel is directed through partial trip valve 104 to at least one of the plurality of burners 103. The burners 103 heat firebox 105 and generate hot combustion gas ("flue gas") that flows upward through the convection section 106 and then out of the furnace via the flue gas stack 107.

During typical pyrolysis operation, the hydrocarbon feed is conducted via conduit 108 and control valve 109 to a preheating conduit 110 in convection section 106 where the feed is preheated by indirect contact with hot flue gas generated by burners 103.

A plurality of feed conduits 111 are arranged in parallel. Although not shown, each of the plurality of feed conduits 111 may be provided with a control valve 109. Each of the plurality of conduits 111 is in fluid communication with a corresponding preheating conduit (not shown) in parallel to preheating conduit 110 in convection section 106. The use of the term "plurality of conduits" is meant to refer to the fact that the convection section 106 is arranged wherein each multiple preheating conduit bank has at least two conduits in parallel. Four conduits are represented in FIG. 1, although the invention encompasses furnaces having 3, 4, 6, 8, 10, 12, 16, or 18 parallel conduits or more.

After the preheated hydrocarbon feed exits the preheating conduit 110, the preheated hydrocarbon feed is mixed with dilution steam. Dilution steam is provided via conduit 112 through control valve 113 to steam preheating conduit 114 in convection section 106 where the dilution steam is preheated by indirect contact with hot flue gas. Dilution steam is added to provide the amount of $H_2O$ required to achieve the desired hydrocarbon partial pressure during pyrolysis reaction. A plurality of steam conduits 115 may be provided corresponding to the plurality of feed conduits 111.

The mixture of dilution steam and preheated hydrocarbon feed is conducted via conduit 116 to heat exchange conduit 117 in convection section 106. A plurality of heat exchange conduits (not shown) may be provided.

Upon exiting the heat exchange conduit 117, the heated mixture is passed to radiant tube 118 in the radiant section of firebox 105 for thermal cracking of the hydrocarbon. A plurality of radiant tubes (not shown) may be provided. The temperature of the heated mixture exiting conduit 117 is generally designed to be at or near the point where significant thermal cracking commences. For a feed where the hydrocarbon is substantially composed of ethane, this can correspond to a temperature of 840° C. to 900° C.

After the desired degree of thermal cracking has been achieved, the furnace effluent is rapidly cooled. For this purpose, the furnace effluent is conducted to one or a series of more than one indirect transfer line heat exchanger(s) ("TLE") 119 where the heat energy from the furnace effluent is indirectly transferred to heat water provided via conduit 120 to produce high pressure steam conducted away via conduit 121. This technique is generally favored as the high pressure steam produced may be further superheated and used to power steam-turbines useful in the process to separate and recover ethylene from the furnace effluent.

The partially cooled furnace effluent leaving TLE 119 is conducted via conduit 122 to quench system 123. Quench system 123 may be any suitable system for cooling the partially cooled furnace effluent. An example of a suitable quench system 123 can be a water quench system where the partially cooled effluent is indirectly quenched with water. For example, water may be provided via conduit 124 and valve 125. The heated water stream exits the quench system 123 via conduit 126. Cooled furnace effluent may be provided to downstream recovery and/or purification processes (not shown) via conduit 127. The temperature of the cooled furnace effluent in conduit 127 can be appropriate for feeding downstream separation equipment, for example, a primary fractionator (not shown) that receives furnace effluent at about 288° C. to 315° C.

Figure 2:
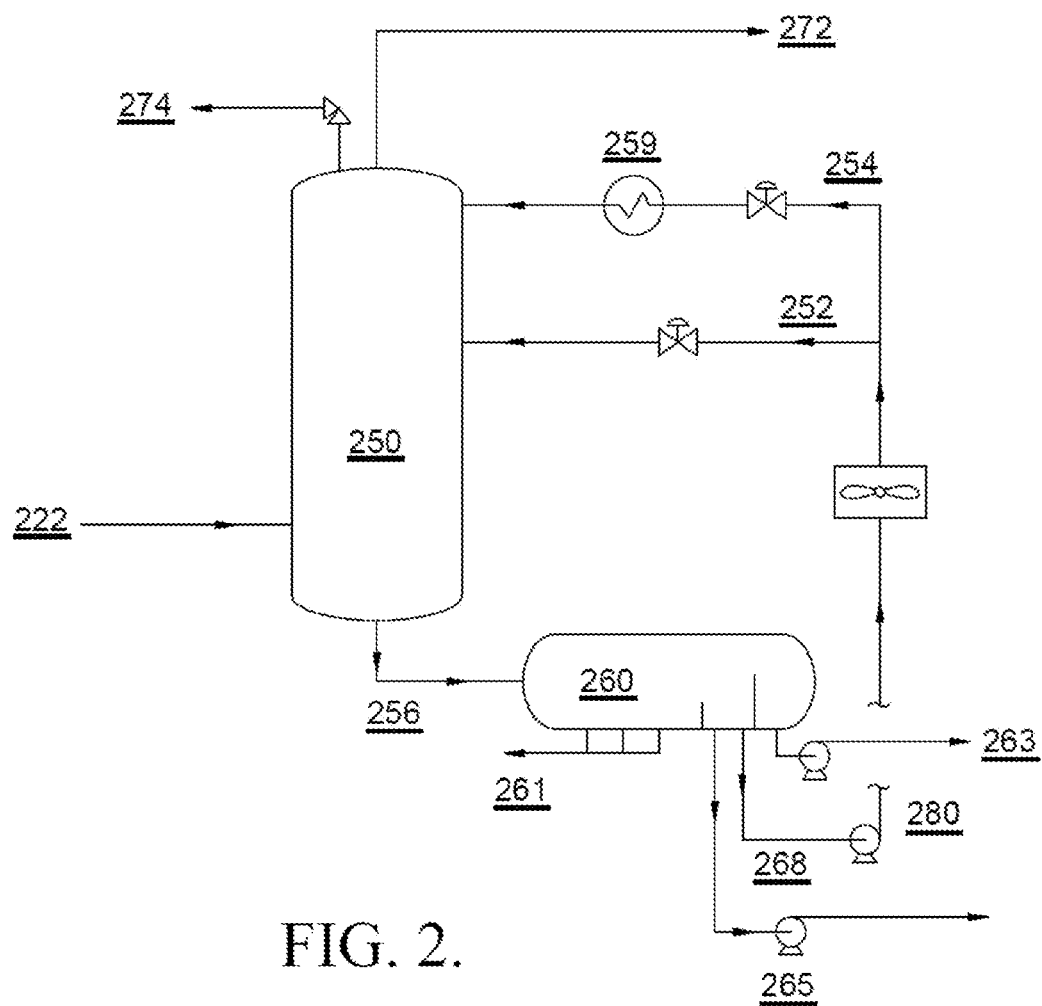
FIG. 2 schematically shows an example of a quench system for use in conjunction with a steam cracker furnace.

Additional details regarding the water quench system 123 are shown in FIG. 2. The quench system includes a quench tower 250, a quench water settler 260, and various other conduits and components. In FIG. 2, conduit 222 carries partially cooled furnace effluent into the quench tower 252. Additionally, one or more water conduits can be used to add quench water to the quench tower 250. In the example shown in FIG. 2, two water conduits 252 and 254 can provide quench water to quench tower 250 as shown. Water conduit 254 is shown as including an additional heat exchanger 259 to allow for a difference in temperature between water conduit 252 and 254. In other aspects, a heat exchanger can be included in water conduit 252 in place of and/or in addition to the heater exchanger 259.

The outputs from water tower 250 can include a heavy fraction 256 that exits from the bottom of the tower and one or more light fractions containing the desired ethylene product, such as light fraction 272. In aspects where the feed to the process tubes of the steam cracker is substantially composed of ethane, a portion of the feed can still correspond to heavier feed compounds. This can result in formation of some heavier products during steam cracking. These heavier products can be included in heavy fraction 256, and subsequently separated out in quench water settler 260. For example, quench water settler 260 can produce one or more tar and/or fuel oil products 261, one or more fuel products 263 (such as pyrolysis gasoline, pumped away, as shown), one or more process condensate products 265 (pumped away, as shown), and a quench water output 268. The quench water output 268 can be passed into one or more quench water pumps 280 for recirculation back to quench water tower 250.

During normal operation, the water tower 250 can generate a light fraction 272 that is sent to a process gas compressor (not shown). However, when a partial trip occurs (such as when the process gas compressor shuts down and prevents flow of light fraction 272), it may be desirable to instead vent 274 the light product output from water tower 250 to a ground flare.

Returning to FIG. 1, to mitigate the effects of thermal shock as may occur when firing is reduced in response to a blower shut-off event and/or other partial trip event, flue gas stack 107 is configured to receive flue gas through one or both of a blower 130 or a blower bypass conduit 131. The flow of flue gas through blower 130 and blower conduit 129 is controlled with a first damper 128 configured and modulated to control pressure inside the furnace. The blower 130 may be of any suitable design. In some embodiments, blower 130 is a double suction, single discharge fan. The furnace 1 includes a blower bypass conduit 131 in fluid communication with flue gas stack 107. Preferably, the blower bypass conduit 131 is the same diameter as the flue gas stack 107. More preferably, the blower bypass conduit 131 is a portion of the flue gas stack 107. The blower bypass conduit 131 includes a second damper 132 configured to control the flow of flue gas there through. First and second dampers 128, 132 may independently be selected according to design requirements. Non-limiting examples of suitable dampers include butterfly or louvre type dampers. Flue gas stack 107 may be of any suitable design. Under normal operating conditions the first damper 128 is in an open position and the second damper 132 is in a closed position allowing at least a portion of the flue gas to pass through the blower 130. In response to a blower shut off event, second damper 132 may be opened allowing at least a portion of the flue gas to be directed through blower bypass conduit 131.

In order to generate sufficient natural draft to permit enough flue gas generation and maintain radiant tube temperature, the height (measured from the end of the furnace convection section to the top of the flue gas stack) of flue gas stack 107 may be determined according to design principles. Generally, a taller flue gas stack will have a more negative pressure. In particular embodiments, flue gas stack 107 may be ≥5 m, e.g., ≥20 m, ≥30 m, ≥40 m, ≥50 m, or ≥60 m. Additionally or alternatively, the height of the flue gas stack 107 may be ≤65 m, e.g., ≤55 m, ≤45 m, ≤35 m, ≤25 m. Particular ranges of the flue gas stack length include ranges formed by any pair of the above-enumerated values, e.g., 5 to 65 m, 20 to 55 m. Preferably the flue gas stack is ≥30 m tall.

Under normal operation, the first damper 128 and/or the blower 130 are configured such that the flow of flue gas through blower conduit 129 is greater than the flow of gas through the blower bypass conduit 131, e.g., the second damper 132 may be closed. The dampers 128 and 132 as well as blower 130 may be in electrical communication with one or more control systems (not shown) including at least one sensor/detector 133 configured to sense one or more parameters characteristic of a blower shut-off event (e.g., pressure, electrical current, blower speed, etc.). Sensor 133 may be of any suitable type. When one or more of the control systems sense an imminent or present blower shut-off event, second damper 132 is moved to a more open position allowing flue gas flow through blower bypass conduit 131. Optionally, first damper 128 may be moved to a more closed position to further direct flue gas flow through blower bypass conduit. Draft pressure may be controlled using second damper 132 or another damper (not shown) in flue gas stack 107. In a particular embodiment, control system opens the second damper 132 when the detector 133 detects a blower shut-off event.

Redirecting flue gas through the natural draft blower bypass conduit 131 and flue gas stack 107 generally will not generate as much draft as when flue gas is routed via an operational blower 130. The firing rate (amount of flue gas generated) must be reduced. Advantageously, a furnace configured with a tall flue gas stack according to the invention permits sufficient flue gas generation to maintain radiant tube temperature. For example, upon sensing that the parameter predictive of a blower shut-off event has exceeded the predetermined value, the control system may close the first damper 128 and open the second damper 132. The control system also reduces the firing rate of the burners 103 to a level that maintains the radiant tubes at temperature to avoid thermal shock that would otherwise occur in a total furnace shutdown.

It is noted that the system shown in FIG. 1 corresponds to a furnace with an outboard induced draft fan (corresponding to blower 130 in a side conduit 129) and a "straight-through" bypass stack (corresponding to conduit 131) with a normally-closed bypass damper 132. Although other configurations are within the scope of the invention, this type of configuration can be beneficial when the blower fan driver is an electric motor. A common cause of loss of quench water circulation to the water quench tower is loss of electrical power to the quench water circulation pumps. For the system to remain operable during such an electric power loss, a furnace would need to be able to sustain the low-firing partial trip condition without the induced draft fan in operation. A configuration similar to the configuration in FIG. 1 makes this possible with the natural draft generated by the "straight-through" stack (once the bypass damper has opened). The required stack height for the conduit 131 can be a function of the convection section pressure drop and the flue-gas temperature achieved in a partial firing trip scenario. Note that the stack height required is increased for furnaces equipped with Selective Catalytic reduction (SCR) units for NOx reduction. SCR catalyst beds add pressure drop to the flue-gas flow path and hence require taller stacks to sustain operation without the induced draft fan in operation.

The control system may reduce the heat input to the furnace, by for example, automatically shutting off only a number of burners in the furnace, e.g., by initiating a partial trip. For example, the control system may close or partially close partial trip valve 104 to reduce the amount of fuel provided through the valve 104 to one or more of the burners 103. In exemplary embodiments, the firing rate can be reduced such that amount of fuel used to heat the firebox during a blower shut-off event (by reduction in the number of burners that are operated and/or in the amount of fuel provided to the burners) is ≤50 wt. %, e.g., ≤30 wt. %, or ≤15 wt %, of the fuel used to operate the burners under normal operating conditions when the blower is functioning. Additionally or alternately, the amount of fuel delivered to the furnaces per unit time (fuel rate) can correspond to 10% to 40% of the amount of fuel (based on heating value) delivered to the furnaces during normal operation, or 20% to 33%.

Under such a reduced firing rate, sufficient heat can be provided to keep the tubes above about 538° C. (1000° F.), preferably above 700° C. (~1300° F.) to avoid undergoing thermal shock. For example, the heat provided to the process tubes can be sufficient to maintain the process tubes at a temperature between about 538° C. (1000° F.) to about 815° C. (~1500° F.), or about 538° C. to about 788° C. (1450° F.), or about 700° C. (~1300° F.) to about 815° C. (~1500° F.), or about 700° C. (~1300° F.) to about 788° C. (~1450° F.). Additionally, the amount of flue gas can kept below ambient pressure by the natural draft of the flue gas stack through the second damper 132 and blower bypass conduit 131. Optionally, the control system may start a timer at the outset of the partial trip. If after a preset time the pressure inside the furnace is not below atmospheric pressure, the control system may stop the flow of all fuel to the furnace. For example, the control system may close shut-off valve 101 if the pressure inside the furnace is not below atmospheric pressure a preset amount of time after firing is partially reduced and flue gas is directed through blower bypass conduit 131.

It is noted that furnaces capable of operating at least partially with natural draft, such as the furnace shown in FIG. 1, are not preferred in many types of conventional steam cracking because tall stacks are needed to provide sufficient draft to meet the desired firing rate or rate of heat generation. Many conventional steam cracking furnaces are designed to use a fan or blower as the means of generating draft and have only a short stack located at the discharge of the blower. In these conventional cases, if the blower ceases operation, either due to mechanical issues or loss of the driving power source, the furnace will lose draft. The flue gas pressure inside the furnace will rise to above ambient pressure. It is normal practice to have pressure sensors located on the furnace which identify when the pressure rises above ambient pressure, and an automatic trip or safety-interlock system that will shut off the fuel supply to the furnace in such a situation. If the full fuel supply is shut off substantially instantaneously, the furnace temperatures will cool down rapidly, including the temperatures of the radiant tubes. This rapid cool down, by itself, is detrimental to service life of the tubes as contraction and expansion lead to metal fatigue. Moreover, the metal fatigue is exacerbated by the presence of coke formed inside tube walls.

Examples of Furnace Partial Trip Conditions

In various aspects, the furnace trip logic can differentiate between a partial firing trip occurring with a loss of quench water circulation, and a partial firing trip occurring due to a furnace-only issue. This can be achieved in various ways. In some aspects, a time delay can be used between sensing a non-sustainable furnace operation condition and sending a partial-trip signal to the furnace. For example, if a high bridgewall pressure is sensed on an individual furnace, a 60-second time delay is typically used after which the furnace is sent to its steam-partial trip condition. Similarly, if a process coil outlet temperature is detected that is greater than a threshold amount, a 60-second delay can enacted before sending the furnace to the steam-partial trip condition. However, if both a) the furnace senses a high bridgewall pressure and b) the trip PLC (programmable logic controller) detects a loss of quench water circulation before the 60-second delay has expired, the trip system can conclude that there is a condition requiring a partial furnace trip without waiting for the 60-second delay period to complete. The furnace can then be set to a partial firing condition with ethane feed still flowing through the furnace and dilution steam at the normal dilution steam to feed ratio. In other aspects, various other conditions can be used, either alone or in combination, to start a delay period for performing a partial trip and/or perform a partial trip without waiting for a delay period to complete.

Detection of Loss of Quench Water Circulation

In various aspects, a variety of methods are available to detect loss of quench water circulation. Such methods include, but are not limited to, a high quench water tower overhead temperature, a low quench tower oil flow rate, and a low quench water pump discharge pressure. In some aspects, it can be preferable to detect loss of quench water circulation rate by measuring quench water pump discharge pressure and inferring loss of quench water circulation when the pressure drops below a pre-determined threshold value. The value used can depend on the specifics of the quench water pumps employed in a given application. One benefit of using pump the quench water pump discharge pressure to detect a loss of quench water circulation can be based on the rapid decline in pump discharge pressure that will occur after quench water pumps lose power. Additionally or alternately, pressure can be reliably measured in ways that are simplified relative to the methods and/or equipment that is required for determining a flow rate of the quench water. Further additionally or alternately, pressure can be readily measured at multiple locations that should have substantially the same pressure and/or defined pressure relationships. In some aspects, multiple pressure measurements can be performed, and detection of a loss of quench water circulation can be based on at least two of the three pressure measurements being below the threshold value for each type of measurement. This type of system logic for determining a trip can provide a reliable method for triggering a partial trip when a pressure loss occurs while reducing or minimizing the likelihood of triggering a partial trip due to a sensor error.

Examples of Partial Trip Conditions

The following examples are prophetic examples based on representative flow rates for commercial scale systems.

In a first example, the conventional "steam partial trip" for a steam cracker furnace can include reducing the firing rate of the furnace to 10% to 40% of the normal operating value, while changing the feed to the process tubes to only dilution steam. During a conventional steam partial trip, the dilution steam rate would be 55 klb/hr (~25,000 kg/hr) per furnace. The corresponding furnace firing rate would correspond to roughly 90 MBtu/hr (~95 GJ/hr). For this type of steam cracker, the conventional steam partial trip can be modified to use a mixture of ethane and steam as the feed to the process tubes. The same furnace firing rate of roughly 90 MBtu/hr (~95 GJ/hr) can be used. For the feed to the process tubes, the feed can correspond to a combination of an ethane feed rate of 45 klb/hr (~21,000 kg/hr) per furnace and a dilution steam rate of 15 klb/hr (~6800 kg/hr) per furnace. In this example, a feed composed of 100% ethane would be used. Alternatively, the hydrocarbon portion of the feed can correspond to a feed that is substantially composed of ethane.

The conditions in the first example for the conventional steam partial trip and the modified partial trip can result in different requirements for supplemental hydrocarbon addition in the ground flare associated with the steam cracker. During a conventional steam partial trip as described above, once any hydrocarbons remaining in the process tube at the start of the partial trip are exhausted, maintaining a target flare gas heating value during the partial trip would require 165 klb/hr (~75,000 kg/hr) of ethane enrichment per furnace. In other words, the entire flare gas heating value would need to be provided from the supplemental ethane addition (or other hydrocarbon addition) to the flare gas. By contrast, in the modified partial trip described above, the combination of ethane and steam delivered to the process tubes during the partial trip has a sufficient energy density so that no additional fuel is needed. Therefore, the partial trip conditions reduce the amount of ethane required for each furnace by ~120 klb/hr (~54,000 kg/hr). In an example where a set of process tubes has 8 associated furnaces, this can correspond to a roughly order of magnitude reduction in the amount of fuel consumed during a partial trip event.

In a second example, the conventional "steam partial trip" for a second steam cracker furnace can include reducing the firing rate of the furnace to 10% to 40% of the normal operating value, while changing the feed to the process tubes to only dilution steam. During a conventional steam partial trip for the second furnace, the dilution steam rate would be 50 klb/hr (~23,000 kg/hr) per furnace. The corresponding furnace firing rate would correspond to roughly 80 MBtu/hr (~85 GJ/hr). For this second type of steam cracker, the conventional steam partial trip can be modified to use a mixture of ethane and steam as the feed to the process tubes. The same furnace firing rate of roughly 80 MBtu/hr (~85 GJ/hr) can be used. For the feed to the process tubes, the feed can correspond to a combination of an ethane feed rate of 70 klb/hr (~32,000 kg/hr) per furnace and a dilution steam rate of 21 klb/hr (~9500 kg/hr) per furnace. In this second example, a feed composed of 100% ethane would be used. Alternatively, the hydrocarbon portion of the feed can correspond to a feed that is substantially composed of ethane.

The conditions in the second example for the conventional steam partial trip and the modified partial trip can result in different requirements for supplemental hydrocarbon addition in the ground flare associated with the steam cracker. During a conventional steam partial trip, once any hydrocarbons remaining in the process tube at the start of the partial trip are exhausted, maintaining a target flare gas heating value during the partial trip would require 166 klb/hr (~75,000 kg/hr) of ethane enrichment per furnace. In other words, the entire flare gas heating value would need to be provided from the supplemental ethane addition (or other hydrocarbon addition) to the flare gas. By contrast, in the modified partial trip described above, the combination of ethane and steam delivered to the process tubes during the partial trip has a sufficient energy density so that no additional fuel is needed. Therefore, the partial trip conditions reduce the amount of ethane required for each furnace by ~96 klb/hr (~44,000 kg/hr). In an example where a set of process tubes has 8 associated furnaces, this can correspond to a roughly order of magnitude reduction in the amount of fuel consumed during a partial trip event.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for operating a steam cracker, comprising:
combusting fuel comprising a first fuel heating value in one or more burners of a steam cracker furnace to form a first flue gas, the furnace comprising a plurality of process tubes;
passing a first feed comprising ethane and steam to the plurality of process tubes at a process tube inlet temperature of about 840° C. or more to form a product comprising ethylene, a volume ratio of steam to hydrocarbon in the feed being about 0.2 to about 0.5;
separating an ethylene-containing stream from the product comprising ethylene in a water quench system;
detecting a condition indicating a partial furnace trip is required;
combusting, based on the detected condition, fuel comprising a second fuel heating value in the one or more burners to form a second flue gas, the second fuel heating value being 10% to 40% of the first fuel heating value;
passing, based on the detected condition, a second feed comprising ethane and steam into the plurality of process tubes at a process tube inlet temperature of about 538° C. or more to produce an exit stream comprising ethane and steam, a volume ratio of steam to hydrocarbon in the second feed being about 0.2 to about 0.5, a ratio of a volume flow rate of the second feed relative to a volume flow rate of the first feed being about 0.3 to about 0.6; and
directing at least a portion of the exit stream to a ground flare system.

2. The method of claim 1, wherein the second feed comprising ethane and steam comprises a ratio of steam to hydrocarbon that is the same as the ratio of steam to hydrocarbon in the first feed.

3. The method of claim 1, wherein the second feed is passed into the plurality of process tubes at a temperature of 538° C. to 815° C.

4. The method of claim 1, wherein the first feed is substantially composed of ethane and steam, and wherein the second feed is substantially composed of ethane and steam.

5. The method of claim 1, wherein the first feed comprises 90 wt % or more of ethane relative to a weight of $C_{2+}$ hydrocarbons in the first feed, wherein the second feed comprises 90 wt % or more of ethane relative to a weight of $C_{2+}$ hydrocarbons in the second feed, or a combination thereof.

6. The method of claim 1, further comprising:
flowing the first flue gas to a flue gas stack exit via a blower; and
flowing at least a portion of the second flue gas to the flue gas stack exit through a blower bypass conduit, the blower bypass conduit being in fluid communication with the flue gas stack exit during the directing.

7. The method of claim 1, wherein the steam cracker furnace further comprises a flue gas stack having a height of about 20 m to about 65 m.

8. The method of claim 1, wherein the ratio of the volume flow rate of the second feed relative to the volume flow rate of the first feed is about 0.3 to about 0.5.

9. The method of claim 1, wherein at least one of the exit stream and the at least a portion of the exit stream has a heating value of about 700 Btu/SCF or more.

10. The method of claim 1, wherein at least one of the exit stream and the at least a portion of the exit stream has a heating value of about 800 Btu/SCF or more.

11. The method of claim 1, further comprising combusting the at least a portion of the exit stream in the ground flare system.

12. The method of claim 11, wherein the at least a portion of the exit stream is combusted in the ground flare system without introducing additional fuel into the ground flare system.

13. The method of claim 11, further comprising introducing additional fuel into the ground flare system, a heating value of the additional fuel being 25% or less of a heating value of the at least a portion of the exit stream.

14. The method of claim 1, wherein a temperature of the plurality of process tubes during the passing of the second feed into the plurality of process tubes is 538° C. to 730° C.

15. The method of claim 1, wherein the detected condition indicates at least one of:
(i) one or more parameters characteristic of a blower shut-off event, the blower being used to conduct the first flue gas to a flue gas stack exit,
(ii) a bridgewall pressure within the furnace exceeds a pre-determined value,
(iii) a process coil outlet temperature is greater than a pre-determined value,
(iv) a loss of quench water circulating within the water quench system, and
(v) a stop in operation of a component downstream from the water quench system.

16. The process of claim 1, wherein the condition indicates one or more parameters characteristic of a blower shut-off event, and wherein the one or more parameters comprise a pressure, an electrical current, a blower speed, or a combination thereof.

17. The method of claim 1, wherein the condition indicates a loss of quench water circulating within the water quench system.

18. The method of claim 17, wherein detecting the loss of quench water circulating within the water quench system comprises:
- detection of a quench tower overhead temperature exceeding a predetermined value;
- detection of a quench tower oil flow rate falling below a predetermined value;
- detection of a pressure within the quench water system in at least three locations with at least two of the three locations being below a predetermined value for the respective location;
- detection of a quench water pump discharge pressure dropping below a pre-determined value;
- or a combination thereof.

19. The method of claim 1, wherein the condition indicates a stop in operation of a component downstream from the water quench system.

20. The method of claim 19, wherein the component comprises a process gas compressor, and wherein detecting the condition comprises detecting an increase in a pressure associated with the process gas compressor.

\* \* \* \* \*